US005576042A

United States Patent [19]

Fuisz

[11] Patent Number: 5,576,042
[45] Date of Patent: Nov. 19, 1996

[54] HIGH INTENSITY PARTICULATE POLYSACCHARIDE BASED LIQUIDS

[75] Inventor: Richard C. Fuisz, Great Falls, Va.

[73] Assignee: Fuisz Technologies Ltd., Chantilly, Va.

[21] Appl. No.: 205,026

[22] Filed: Mar. 2, 1994

Related U.S. Application Data

[63] Continuation of Ser. No. 782,430, Oct. 25, 1991, abandoned.

[51] Int. Cl.$^6$ ........................................................ A23L 1/236
[52] U.S. Cl. ............................................. 426/548; 426/590
[58] Field of Search ...................................... 426/590, 548

[56] References Cited

U.S. PATENT DOCUMENTS

| | | |
|---|---|---|
| Re. 32,016 | 10/1985 | Esders et al. . |
| 796,528 | 8/1905 | Pollock . |
| 816,055 | 3/1906 | Zoeller . |
| 847,366 | 3/1907 | Pollock . |
| 856,424 | 6/1907 | Robinson . |
| 1,489,342 | 4/1924 | Brent . |
| 1,541,378 | 6/1925 | Parcell . |
| 2,826,169 | 3/1958 | Le Veen . |
| 2,918,404 | 12/1959 | Mende et al. . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,118,396 | 1/1964 | Brown et al. . |
| 3,118,397 | 1/1964 | Brown et al. . |
| 3,125,967 | 3/1964 | Bowe . |
| 3,131,428 | 5/1964 | Mika . |
| 3,308,221 | 3/1967 | Opfell . |
| 3,324,061 | 6/1967 | Tanquary et al. . |
| 3,482,998 | 12/1969 | Carroll et al. . |
| 3,523,889 | 8/1970 | Eis . |
| 3,557,717 | 1/1971 | Chivers ................................ 426/660 |
| 3,557,718 | 1/1971 | Chivers ................................ 426/658 |
| 3,595,675 | 7/1971 | Ash et al. . |
| 3,615,671 | 10/1971 | Groesbeck ........................... 426/658 |
| 3,625,214 | 12/1971 | Higuchi . |
| 3,676,148 | 7/1972 | De Weese et al. . |
| 3,686,000 | 8/1972 | Lawrence ............................. 99/134 |
| 3,723,134 | 3/1973 | Chivers ................................ 426/660 |
| 3,749,671 | 7/1973 | Gedge et al. . |
| 3,762,846 | 10/1973 | Chivers . |
| 3,766,165 | 10/1973 | Rennhard . |
| 3,856,443 | 12/1974 | Salvi . |
| 3,875,300 | 4/1975 | Homm et al. . |
| 3,876,794 | 4/1975 | Rennhard . |
| 3,882,725 | 5/1975 | Rao et al. . |
| 3,902,351 | 9/1975 | Kreps . |
| 3,907,644 | 9/1975 | Möllering et al. . |
| 3,912,588 | 10/1975 | Möllering et al. . |
| 3,925,164 | 12/1975 | Beucamp et al. . |
| 3,925,525 | 12/1975 | LaNieve . |
| 3,930,043 | 12/1975 | Warning et al. . |
| 3,951,821 | 4/1976 | Davidson . |
| 3,967,623 | 7/1976 | Butterworth et al. . |
| 3,972,725 | 8/1976 | Nicol . |
| 3,981,739 | 9/1976 | Dmitrovsky et al. . |
| 3,991,766 | 11/1976 | Schmitt et al. . |
| 3,992,265 | 11/1976 | Hansen . |
| 4,056,364 | 11/1977 | Dmitrovsky et al. . |
| 4,072,658 | 2/1978 | Okamoto et al. . |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0287488A1 | 3/1988 | European Pat. Off. . |
| 0387950A1 | 8/1990 | European Pat. Off. . |
| 86052 | 4/1988 | Israel . |
| 86053 | 4/1988 | Israel . |
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 90/8406 | 8/1991 | South Africa . |
| 519858 | 5/1971 | Switzerland . |
| 489211 | 7/1986 | Switzerland . |
| 2155934 | 3/1985 | United Kingdom . |
| WO91/18613 | 12/1991 | WIPO . |

OTHER PUBLICATIONS

Kiyushi Kurihara, "Patent Abstracts of Japan", vol. 011, No. 326, (c–454) Oct. 23, 1987.
R. H. Doremus, "Crystalliazation of Sucrose From Aqueous Solution," *Journal of Colloid and Interface Science*, 104, pp. 114–120 (1985).
P. Bennema, "Surface Diffusion and the Growth of Sucrose Crystals, " *Journal of Crystal Growth*, 3,4 pp. 331–334 (1968).
T. D. Simpson, et al., "Crystalline Forms of Lactose Produced in Acidic Alcoholic Media," *Journal of food Science*, 47, pp. 1948–1954 (1982).
A. D. Randolph, et al., "Continuous Sucrose Nucleation," *The International Sugar Journal*, pp. 8–12 (1974).
K. B. Domovs, et al., "Methanol–Soluble Complexes of Lactose and of other Carbohydrates," *J. Dairy Science*, 43, pp. 1216–1223 (1960).
A. D. Randolph, et al., "Continuous Sucrose Nucleation," *The International Sugar Journal*, pp. 35–38 (1974).
A. D. Randolph, et al., "Continuous Sucrose Nucleation," *The International Sugar Journal*, pp. 73–77 (1974).
ICI Americas, Inc., "ICI Americas Products for Cosmetics and Pharmaceuticals," (1977).
Domino Sugar Corporation, "Co–crystallization" product pamplet.
Domino Sugar Corporation, "Raspberry" product pamplet.
Domino Sugar Corporation, "Molasses Dark" product pamplet.

*Primary Examiner*—Carolyn Paden
*Attorney, Agent, or Firm*—Hoffmann & Baron

[57] ABSTRACT

High intensity matrix formed from melt-spinning flavor and/or sweetener with a carrier material capable of being spun is disclosed for flavoring liquids. The matrix is rapidly soluble and autogeneously forms a uniform, colloidal-like suspension.

25 Claims, No Drawings

U.S. PATENT DOCUMENTS

| | | |
|---|---|---|
| 4,086,418 | 4/1978 | Turbak et al. . |
| 4,090,920 | 5/1978 | Studer, Jr. . |
| 4,136,145 | 1/1979 | Fuchs et al. . |
| 4,153,512 | 5/1979 | Messner et al. . |
| 4,159,210 | 6/1979 | Chen et al. . |
| 4,160,696 | 7/1979 | Wu . |
| 4,164,448 | 8/1979 | Röeschlau et al. . |
| 4,166,005 | 8/1979 | Masurekar et al. . |
| 4,168,205 | 9/1979 | Danninger et al. . |
| 4,178,393 | 12/1979 | Gregersen . |
| 4,186,251 | 1/1980 | Tarbutton . |
| 4,194,063 | 3/1980 | Frank et al. . |
| 4,199,373 | 4/1980 | Dwivedi . |
| 4,241,178 | 12/1980 | Esders et al. . |
| 4,271,199 | 6/1981 | Cherukuri et al. . |
| 4,293,292 | 10/1981 | Israel . |
| 4,293,570 | 10/1981 | Vadasz . |
| 4,303,684 | 12/1981 | Pitchon et al. . |
| 4,335,232 | 6/1982 | Irwin . |
| 4,338,350 | 7/1982 | Chen et al. . |
| 4,348,420 | 9/1982 | Lynch et al. . |
| 4,362,757 | 12/1982 | Chen et al. . |
| 4,371,516 | 2/1983 | Gregory et al. . |
| 4,376,743 | 3/1983 | Dees . |
| 4,382,963 | 5/1983 | Klose et al. . |
| 4,382,967 | 5/1983 | Koshida . |
| 4,492,685 | 1/1985 | Keith et al. . |
| 4,496,592 | 1/1985 | Kuwahara et al. . |
| 4,500,546 | 2/1985 | Turbak et al. . |
| 4,501,538 | 2/1985 | Bray . |
| 4,511,584 | 4/1985 | Percel et al. . |
| 4,526,525 | 7/1985 | Oiso et al. . |
| 4,581,234 | 4/1986 | Cherukuri et al. . |
| 4,585,797 | 4/1986 | Cioca . |
| 4,619,833 | 10/1986 | Anderson . |
| 4,684,534 | 8/1987 | Valentine . |
| 4,722,845 | 2/1988 | Cherukuri et al. . |
| 4,747,881 | 5/1988 | Shaw et al. . |
| 4,765,991 | 8/1988 | Cherukuri et al. . |
| 4,772,477 | 9/1988 | Weiss et al. . |
| 4,793,782 | 12/1988 | Sullivan . |
| 4,797,288 | 1/1989 | Sharma et al. . |
| 4,816,283 | 3/1989 | Wade et al. . |
| 4,839,184 | 6/1989 | Cherukuri et al. . |
| 4,846,643 | 7/1989 | Yamamoto et al. . |
| 4,853,243 | 8/1989 | Kahn et al. . |
| 4,855,326 | 8/1989 | Fuisz . |
| 4,867,986 | 9/1989 | Desai et al. . |
| 4,871,501 | 10/1989 | Sugimoto et al. . |
| 4,872,821 | 10/1989 | Weiss . |
| 4,873,085 | 10/1989 | Fuisz . |
| 4,879,108 | 11/1989 | Yang et al. . |
| 4,882,144 | 11/1989 | Hegasy . |
| 4,885,281 | 12/1989 | Hanstein et al. . |
| 4,900,563 | 2/1990 | Cherukuri et al. . |
| 4,927,646 | 5/1990 | Jenner ................................. 426/548 |
| 4,931,293 | 6/1990 | Cherukuri et al. . |
| 4,933,192 | 6/1990 | Darling . |
| 4,939,063 | 7/1990 | Tamagawa . |
| 4,978,537 | 12/1990 | Song . |
| 4,981,698 | 1/1991 | Cherukuri et al. . |
| 4,988,529 | 1/1991 | Nakaya et al. . |
| 4,997,856 | 5/1991 | Fuisz . |
| 5,009,893 | 4/1991 | Cherukuri et al. . |
| 5,011,532 | 4/1991 | Fuisz . |
| 5,028,632 | 7/1991 | Fuisz ................................... 426/658 |
| 5,034,421 | 7/1991 | Fuisz . |
| 5,037,662 | 8/1991 | Poulose et al. . |
| 5,039,446 | 8/1991 | Estell . |
| 5,041,377 | 8/1991 | Becker et al. . |
| 5,057,328 | 10/1991 | Cherukuri et al. . |
| 5,066,218 | 11/1991 | Silver . |
| 5,073,387 | 12/1991 | Whistler . |
| 5,077,076 | 12/1991 | Gonsalves et al. . |
| 5,079,027 | 1/1992 | Wong et al. . |
| 5,082,682 | 1/1992 | Peterson . |
| 5,082,684 | 1/1992 | Fung . |
| 5,084,295 | 1/1992 | Whelan et al. . |
| 5,089,606 | 2/1992 | Cole et al. . |
| 5,094,872 | 3/1992 | Furcsik et al. . |
| 5,096,492 | 3/1992 | Fuisz . |
| 5,104,674 | 4/1992 | Chen et al. . |
| 5,110,614 | 5/1992 | Corbin et al. . |
| 5,164,210 | 11/1992 | Campbell et al. . |
| 5,169,657 | 12/1992 | Yatka et al. . |
| 5,169,658 | 12/1992 | Yatka et al. . |
| 5,171,589 | 12/1992 | Richey et al. . |
| 5,173,317 | 12/1992 | Hartman et al. . |
| 5,173,322 | 12/1992 | Melachouris et al. . |
| 5,175,009 | 12/1992 | Synosky et al. . |
| 5,196,199 | 3/1993 | Fuisz . |
| 5,236,734 | 8/1993 | Fuisz . |
| 5,238,696 | 8/1993 | Fuisz . |
| 5,268,110 | 12/1993 | Fuisz . |
| 5,279,849 | 1/1994 | Fuisz et al. . |
| 5,284,659 | 2/1994 | Cherukuri et al. . |
| 5,286,513 | 2/1994 | Fuisz . |
| 5,288,508 | 2/1994 | Fuisz . |
| 5,306,955 | 4/1994 | Fryer . |
| 5,346,377 | 9/1994 | Bogue . |
| 5,348,758 | 9/1994 | Fuisz et al. . |

HIGH INTENSITY PARTICULATE POLYSACCHARIDE BASED LIQUIDS

This is a continuation of application Ser. No. 07/782,430 filed on Oct. 25, 1991, abandoned.

BACKGROUND OF THE INVENTION

The present invention is directed to the use of high intensity particulates as flavorants and/or sweeteners. In particular, the present invention is directed to the use of soluble particulates combined in such a manner so as to optimize the organoleptic characteristics, i.e. flavor and/or sweetness of the material.

Over the years, considerable effort has been directed to improving the taste of beverages. In this regard, various powdered drink mixes have become widely accepted by the consumer as a means for flavoring liquids. Most drink mix powders include granular sucrose, flavoring agents and other materials such as acidulants.

More recently, artificial sweeteners have been proposed to replace the sugar portion of drink mixes and provide lower calorie beverages. For example, U.S. Pat. No. 4,619,833 discloses sugar-free, dry beverage mixes which include a uniform dispersion of a water-soluble food acid, a flavor and a flow conditioner combined with maltodextrin.

Two common problems associated with most powdered drink mixes have been poor solubility of the powdered mix and inadequate dispersal of the flavor/sweetener in the target liquid. As a result, most beverages prepared with granular mixes have provided at best only adequate flavor and/or sweetness impact.

The rapid solubility of cotton candy made from sucrose is known by all who have eaten it. This desirable property has not gone unnoticed by those seeking to flavor and/or sweeten beverages. For example, U.S. Pat. No. 3,615,671 discloses a blanket spun from a mixture of sucrose and a humectant encasing dry food particles to flavor beverages. Unlike typical powder drink mixes, most of the sugar is in the form of spun filaments which enrobe the beverage mix ingredients. The '671 patent, however, fails to address the problem of adequately dispersing the remaining drink mix ingredients which are merely deposited on the spun blanket and thus maintain their inherent physical properties.

In spite of the above-described efforts, improvements in flavoring and/or sweetening liquids are still sought. The advantageous properties of rapid solubility and colloidal-like dispersability achieved by melt spinning have yet to be applied to many beverage ingredients. For example, several high intensity sweeteners cannot withstand the temperatures heretofore thought to be necessary for melt spinning.

It is therefore an object of the present invention to provide methods and compositions which provide rapidly soluble high intensity particulates which uniformly disperse in the target liquid and provide high flavor impact.

It is a further object of the present invention to include relatively heat sensitive materials, such as high intensity sweeteners, in a rapidly soluble medium without deleteriously effecting the heat sensitive materials.

SUMMARY OF THE INVENTION

The present invention provides a high intensity flavor system having flavor particles for effecting the organoleptic quality of a beverage. Organoleptically perceivable particles such as flavoring agents and/or sweeteners are combined with melt-spinnable carrier materials. When added to a liquid, the high intensity particles are rapidly soluble and provide a dramatically improved flavor and/or sweetness impact.

Flavoring agents may be selected from natural flavors, artificial flavors and mixtures thereof. Sweeteners, on the other hand, may be selected from both natural and artificial sweeteners agents and may include high intensity sweetening agents such as dipeptide sweeteners, saccharin, chloro-derivatives of sucrose such as Sucralose® and the like.

Carrier agents capable of being spun include saccharides such as, for example, sugars. In a preferred embodiment, the melt-spinnable carrier agents include maltodextrins, polydextrose and/or corn syrup solids which can be melt spun at temperatures much lower than most other polysaccharides.

As a result of the present invention, high intensity particulates are provided which are not only rapidly soluble, but also provide superior colloidal dispersions of the flavoring and/or sweetening agents in a liquid. Moreover, since carrier agents such as maltodextrin, corn syrup solids and polydextrose can be spun at temperatures well below that required for sucrose, heat sensitive flavors and/or sweeteners can now be included in high intensity particulates and, therefore, advantageously dispersed in a liquid.

In the past, powder-based drink mixes were inadequately dispersed to obtain the full impact of each particle. The present invention overcomes this difficulty by separating the particles and exposing the entire surface to the liquid upon dissolution of the carrier material. Not only is the intensity of the flavor increased, but uniformity of flavor throughout the liquid is also achieved. Moreover, this optimization can be achieved with little or no agitation.

DETAILED DESCRIPTION OF THE INVENTION

In accordance with the present invention, flavor particles are provided for altering an organoleptic quality such as flavor and/or sweetness of a liquid. The particles are combined with a soluble fiber by spinning the particles with a carrier agent capable of being melt spun.

The spinning process by which the particles are combined with the soluble carrier is preferably carried out with "cotton candy" fabricating equipment. The floss spinning machine used herein can be any cotton candy-type machine, such as the Econofloss Model 3017 manufactured by Gold Metal Products Company of Cincinnati, Ohio. It will be appreciated by those skilled in the art from the present description that any apparatus or physical process which provides similar shear forces and temperature gradient conditions can also be used. For simplicity in disclosing and describing this invention, the term "melt-spinning" will be understood to mean that combination of temperature, shear flow, flow rates, mechanical forces and thermal gradients through the processing which are of the type exerted by operation in the cotton candy type machine.

The flavor particles, which for the purpose of the present invention include both flavoring agents and sweeteners, are uniquely combined with the carrier material such that the spun product has a substantially uniform consistency of soluble carrier and particles. The resulting spun mass provides a highly soluble matrix with flavor particles separated for universal exposure of its surface to the receiving liquid. This results in an immediate and intense flavor release into the liquid.

Melt spinnable carrier materials include, for example, sugars such as sucrose, maltose, fructose, glucose and lactose. Other carrier materials can be selected from maltodextrins, polydextrose, corn syrup solids and mixtures thereof. These latter carrier materials can be spun at temperatures well below that of other polysaccharides and permit the artisan to include heat sensitive sweetening agents and/or flavoring agents, particularly high intensity sweetening agents, such as aspartame, in the spun product.

Maltodextrin is available in various dextrose equivalent (de) ratios. Ratios of maltodextrins with de ratios greater than 20 are also referred to as corn syrup solids.

Polydextrose is an essentially non-nutritive carbohydrate substitute (1 cal/gm) which can be prepared through polymerization of glucose in the presence of food-acceptable polycarboxylic acid catalysts and polyols. See, for example, U.S. Pat. No. 3,766,165 and U.S. Pat. No. 3,874,794. Generally, polydextrose is known to be commercially available in three forms. Polydextrose A and Polydextrose K are powdered solids, while Polydextrose N is supplied as a 70% solution.

The spinning process for producing highly soluble "cotton candy" is a melt extrusion process. The stock material, historically sucrose, is melted and forced through spinerettes. Conventional equipment includes a rotating spinning head surrounded by a bowl into which the fibers are spun. Typically, the temperature of the grid in the spinning machine required for spinning sucrose is from about 180° F. to about 266° F. at operating speeds of about 3500 RPM.

While many flavor particles can be prepared for the high intensity flavor system of the present invention at the above-mentioned temperatures, it has been unexpectedly discovered that the flavor system can also be prepared at much lower temperatures by using maltodextrins, corn syrup solids and polydextrose. For example, a melt spun flavor particle-bearing matrix is readily obtainable with these carrier materials at operating temperatures as much as 30 to 40% below that required for saccharides such as surose or lactose. This advantageous property permits many heat-sensitive organoleptic materials to safely undergo melt spinning. While not wishing to be bound to any particular theory, it is thought that in addition to the lower melt spinning temperatures required by certain carrier materials, the extremely limited time which flavorant materials are exposed to high temperatures and shear allows a matrix to be formed without exposing flavorant materials for time periods long enough to cause degradation.

For example, aspartame, notoriously unstable at high temperatures, can now be readily included in the novel high intensity flavor system. Aspartame can be protectively spun not only due to the lower temperatures allowed with maltodextrin, corn syrup solids and/or polydextrose, but also due to the short dwell time of the flavorant at high temperature and shear in the melt-spinning apparatus. The present invention, however, is not limited to the protective melt spinning of aspartame with a carrier, since it is understood by those skilled in the art that many heat sensitive flavors and/or sweeteners can avoid the degradation heretofore experienced at such high temperatures.

The organoleptically-perceivable materials included in the high intensity flavor system of the present invention may be selected from sweeteners, flavoring agents and mixtures thereof. With regard to sweeteners, the present invention contemplates the inclusion of both natural and artificial sweeteners. The sweeteners may be chosen from the following non-limiting list: sugars such as sucrose, glucose (corn syrup), dextrose, invert sugar, fructose, and mixtures thereof; saccharin and its various salts such as the sodium or calcium salt; cyclamic acid and its various salts such as the sodium salt; dipeptide sweeteners such as aspartame; dihydrochalcone compounds, glycyrrhizin; Stevia Rebaudiana (Stevioside); chloro derivatives of sucrose such as Sucralose®. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof.

The flavoring agents may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, lime and grapefruit and fruit essences including apple, pear, peach, grape, strawberry, raspberry, cherry, plum, pineapple, apricot and other fruit flavors.

Other useful flavorings include aldehydes and esters such as benzaldehyde (cherry, almond), citral, i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), mixtures thereof, and the like.

The amount of the flavoring agent included in the high intensity particulate is a matter of preference. It is contemplated, however, that the flavoring agent will be present in amounts of from about 0.01 to about 70, preferably from about 0.1 to about 50, and most preferably from about 0.1 to about 35 by weight of the flavor delivery system matrix.

By spinning the above-mentioned organoleptically perceivable flavor particles with the melt spinnable carriers, normally non-water soluble ingredients can be uniformly dispersed when contacted with water. The formation of the matrix is such that when added to a liquid, the particles carried in the matrix disperse to form a colloidal or pseudo-colloidal dispersion. This unique method of dispersing the organoleptic ingredients results in a dramatic flavor impact.

The unique delivery system can also include a colorant. Suitable colorants may be selected from any of the numerous food, drug and cosmetic dyes known as FD&C dyes and the like. Even though colorants for use herein are preferably water-soluble, the normally non-water soluble colorants can also be included when spun with the carrier material. A full recitation of all FD&C and D&C dyes and their corresponding chemical structures may be found in the Kirk-Othmer Encyclopedia of Chemical Technology, in Volume 5, pages 857–884, which is incorporated herein by reference.

In a further aspect of the present invention, the organoleptically perceivable material may include combinations of the above ingredients in the form of processed dry flavor drink mixes. For example, readily available beverage mixes such as KOOLAID® or GATORADE® powders may be combined in a matrix by melt spinning.

The organoleptically-perceivable material(s) and carrier material capable of being spun into fiber form may be combined prior to melt spinning. The ingredients may be combined, for example, by co-crystallization of a solution containing both the carrier and the organoleptically perceivable material(s). Co-crystallization involves combining the ingredients in a heated liquid state and thereafter allowing them to cool in a unified, crystallized manner. The unified structures are then reduced in size such as by being ground before being spun.

Other means of combining organoleptic perceivable materials with the carrier are also contemplated. For example, the carrier and material may be combined in the flossing machine. In some cases, an oleaginous substance such as corn oil or polyvinylpyrrolidone (PVP), can be added to ensure distribution of the particles throughout the matrix of the spun product. For example, a 1% oil or a 2–3% solution of PVP may be added to the ingredients during the melt spinning. Such agents present the particles to the carrier during melt spinning so that as the matrix is formed, the particulate is substantially evenly distributed in the carrier.

The spun matrix which contains the organoleptically perceivable material can also be compacted to less than 50% of the as-spun volume. Preferably, however, the matrix is compacted to less than 30% and most preferably to less than 15% of the as- spun volume. The spun matrix may also be reduced in particle size such as by milling to provide the high intensity particulates.

EXAMPLES

The following examples serve to provide further appreciation of the invention but are not meant in ally way to restrict the effective scope of the invention. Unless indicated otherwise, the Econo-Floss machine referred to above was used to form the spun fiber.

EXAMPLE 1

In this Example, 180 grams of KOOLAID® fruit punch flavor beverage granules were first hand mixed with 20 grams of MAZOLA® corn oil until a somewhat uniform wetting of the granules was obtained. The mixture was then melt spun with the machine operating at the medium setting, about 3500 revolutions per minute (RPM). The resultant matrix was then respun in a bin ring to produce a fine floss. The floss was thereafter compacted to about 25% of the as spun volume and milled to a particle size of about 100 microns.

A 5 gram sample of the floss particulate was then added to 50 ml of tap water at room temperature. Almost immediately, the floss particulate dissolved and formed a colloidal-like dispersion. The resultant beverage was found to have a dramatically improved flavor impact when compared to the beverage prepared with the unspun granules.

EXAMPLE 2

In this Example, 190 grams of GATORADE® lemon-lime flavored drink mix granules were combined with 90 grams of maltodextrin 35-R, a product of the ADM Co. until a uniform mixture was obtained. Thereafter, a 10 gram quantity of MAZOLA® corn oil was geometrically added to mixture using a mortar and pestle. This mixture was then spun at the medium setting, 3500 revolution per minute (RPM) to produce yellow spicules having a crisp flavor and high impact.

EXAMPLE 3

In this Example, the procedure of Example 2 was repeated, except that 150 grams of maltodextrin were combined with the same amount (190 grams) of GATORADE®. This additional amount of maltodextrin caused the spun product to take the form of larger chips rather than the spicules of Example 2. In addition, it was observed that less of the as-spun product stuck to the bin ring. The flavor impact of the chips was not adversely effected by the additional amount of maltodextrin.

EXAMPLE 4

In this Example, 100 grams of polydextrose K powder was co-crystallized with 1 gram of the artificial, high intensity sweetener, aspartame, and 1 gram of citrus flavor oil. Co-crystallization was achieved by dissolving in water and mixing the ingredients until a homogeneous liquid was achieved. The liquid mixture was thereafter dried at a temperature of about 120° F. and allowed to solidify before being ground to particle size. The co-crystallized particles were spun at a low setting to form a fine flake matrix.

5 grams of the flake matrix obtained was placed in 50 ml of water at room temperature and dissolved, forming a colloidal-like suspension. The resultant beverage was tasted and found to have an organoleptically pleasing flavor impact with no evidence of the aspartame breakdown.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A method of enhancing the perception of the organoleptic characteristics of a liquid by achieving rapid and uniform dispersibility of an organoleptically-perceivable material therein comprising the steps of:

providing a solid melt-spun matrix comprising a high intensity organoleptically-perceivable material selected from the group consisting of synthetic sweeteners, synthetic flavor oils, natural flavor oils and mixtures thereof uniformly separated and dispersed throughout a solid water-soluble carrier selected from the group consisting of polydextrose, maltodextrin, corn syrup solids and mixtures thereof;

adding said solid melt-spun matrix to a liquid and allowing said matrix to rapidly and uniformly disperse throughout the liquid thereby providing an intense organoleptic perception of said high intensity organoleptically-perceivable material due to the completeness and intensity of the release of said organoleptically-perceivable material.

2. The method of claim 1, wherein said synthetic sweetener is selected from the group consisting of saccharin, saccharin salts, cyclamic acid, cyclamic acid salts, aspartame, sucralose, acesulfame, and combinations thereof.

3. The method of claim 2, wherein said flavorant is present in an amount of from about 0.01 to about 70% by weight of said matrix.

4. The method of claim 3, wherein said flavorant is present in an amount of from about 0.1 to about 50% by weight of said matrix.

5. The method of claim 4, wherein said flavorant is present in an amount of from about 0.1 to about 35% by weight of said matrix.

6. The method of claim 5, wherein said matrix is compacted to less than 50% of the as spun volume.

7. The method of claim 6, wherein said matrix is compacted to less than 30% of the as spun volume.

8. The method of claim 7, wherein said matrix is compacted to less than 15% of the as spun volume.

9. A matrix comprising high intensity organoleptically-perceivable material united with a solid water-soluble carrier material, said matrix having said high intensity organoleptically-perceivable material substantially uniformly separated and dispersed throughout said carrier material, said matrix being formed by a melt spinning process comprising subjecting said carrier material and said high intensity organoleptically-perceivable material to conditions of shear forces and temperature which form said matrix without causing degradation of said high intensity organoleptically-perceivable material, wherein said high intensity organoleptically-perceivable material is selected from the group consisting of synthetic sweeteners, synthetic flavor oils, natural flavor oils and mixtures thereof and wherein said solid water-soluble carrier material is selected from the group consisting of polydextrose, maltodextrin, corn syrup solids and mixtures thereof.

10. The flavoring matrix of claim 9, wherein said synthetic sweetener is selected from the group consisting of saccharin, saccharin salts, cyclamic acid, cyclamic acid salts, aspartame, sucralose, acesulfame, and combinations thereof.

11. The flavoring matrix of claim 10, wherein said flavorant is present in an amount of from about 0.01 to about 70% by weight of said matrix.

12. The flavoring matrix of claim 11, wherein said flavorant is present in an amount of from about 0.1 to about 50% by weight of said matrix.

13. The flavoring matrix of claim 12, wherein said flavorant is present in an amount of from about 0.1 to about 35% by weight of said matrix.

14. The flavoring matrix of claim 13, wherein said matrix is compacted to less than 50% of the as spun volume.

15. The flavoring matrix of claim 14, wherein said matrix is compacted to less than 30% of the as spun volume.

16. The flavoring matrix of claim 15, wherein said matrix is compacted to less than 15% of the as spun volume.

17. A method of making a solid matrix having high intensity organoleptically-perceivable materials substantially uniformly separated and dispersed throughout a solid water-soluble carrier material, said matrix providing enhanced organoleptic perception and uniform dispersibility of said organoleptically-perceivable material to a liquid medium, said method comprising melt-spinning said carrier material and said high intensity organoleptically-perceivable material by subjecting said carrier material and said organoleptically-perceivable material to conditions of shear force and temperature which form said matrix without causing degradation of said organoleptically-perceivable material; whereby said high intensity organoleptically-perceivable material is selected from the group consisting of synthetic sweeteners, synthetic flavor oils, natural flavor oils and mixtures thereof and is substantially uniformly dispersed throughout and united with said carrier material within said matrix and wherein said carrier material is selected from the group consisting of polydextrose, maltodextrin, corn syrup solids and mixtures thereof.

18. The method of claim 17, wherein said synthetic sweetener is selected from the group consisting of saccharin, saccharin salts, cyclamic acid, cyclamic acid salts, aspartame, sucralose, acesulfame, and combinations thereof.

19. The method of claim 18, wherein said flavorant is present in an amount of from about 0.01 to about 70% by weight of said matrix.

20. The method of claim 19, wherein said flavorant is present in an amount of from about 0.1 to about 50% by weight of said matrix.

21. The method of claim 20, wherein said flavorant is present in an amount of from about 0.1 to about 35% by weight of said matrix.

22. The method of claim 21, wherein said matrix is compacted to less than 50% of the as spun volume.

23. The method of claim 22, wherein said matrix is compacted to less than 30% of the as spun volume.

24. The method of claim 23, wherein said matrix is compacted to less than 15% of the as spun volume.

25. A method of making a beverage product capable of rapidly and uniformly dispersing high intensity organoleptically-perceivable material when placed in water comprising:

forming a melt-spun matrix having said high intensity organoleptically-perceivable material substantially uniformly separated and dispersed throughout a solid water-soluble carrier material, said matrix being formed by subjecting said carrier material and said high intensity organoleptically-perceivable material to conditions of shear forces and temperature which form said matrix without causing degradation of said high intensity organoleptically-perceivable material; and wherein said high intensity material is selected from the group consisting of synthetic sweeteners, synthetic flavor oils, natural flavor oils and mixtures thereof and wherein said carrier material is selected from the group consisting of polydextrose, maltodextrin, corn syrup solids and mixtures thereof; and adding said matrix to water.

\* \* \* \* \*